United States Patent [19]

Botsco et al.

[11] 4,215,583
[45] Aug. 5, 1980

[54] APPARATUS AND METHOD FOR BONDTESTING BY ULTRASONIC COMPLEX IMPEDANCE PLANE ANALYSIS

[75] Inventors: Ronald J. Botsco, Huntington Beach; John E. Todd, Long Beach; Robert L. Jones, La Habra, all of Calif.

[73] Assignee: NDT Instruments, Inc., Huntington Beach, Calif.

[21] Appl. No.: 960,704

[22] Filed: Nov. 14, 1978

[51] Int. Cl.$^2$ ............................................. G01N 29/04
[52] U.S. Cl. ..................................................... 73/582
[58] Field of Search ................. 73/582, 588, 598, 627; 358/112, 110; 340/5 MP; 367/11

[56] References Cited

U.S. PATENT DOCUMENTS

| | | | |
|---|---|---|---|
| 3,512,400 | 5/1970 | Lynnworth | 73/627 |
| 3,564,903 | 2/1971 | Woodmansee et al. | 73/582 |
| 3,832,887 | 9/1974 | Zeutschel | 73/598 |

*Primary Examiner*—Anthony V. Ciarlante
*Attorney, Agent, or Firm*—Fischer and Tachner

[57] ABSTRACT

A non-destructive bond testing apparatus utilizes impedance variation represented by both the phase and amplitude of the signal vector response of a sonic energy generating and receiving probe, which is applied to a laminar, honeycomb or fiber composite structure under test. Typical bonding methods for which this bondtester and method are applicable include adhesive bonding, diffusion bonding, brazing, resistance and impact/friction bonding. A cathode ray tube displays the tip of the vector (as a bright dot) which represents the impedance characteristic affected by the structure under test. A null circuit deletes the response of a non-flawed (or normal) portion of the structure under test so that a flawed (or abnormal) portion of the structure produces an impedance variation from the null point, the variation being represented on a polar coordinate display by the amplitude and angular position of the vector tip, thereby providing diagnostic information regarding the location and type of the bondline condition being detected. Bondline conditions/flaws detectable include, disbonds, adhesive thickness, adhesive porosity, degree of adhesive cure, adhesive (cohesive) strength and forms of in-service adhesive or bondline degradation.

32 Claims, 13 Drawing Figures

APPARATUS AND METHOD FOR BONDTESTING BY ULTRASONIC COMPLEX IMPEDANCE PLANE ANALYSIS

The instrument of the present invention utilizes a sonic-type probe which is applied directly to the surface of the structure under test. The probe is activated with a sine wave oscillator of known frequency, and reflections back to the probe from the structure under test create a standing wave, the amplitude and phase of which are dependent upon the characteristics of the structure including the bondline condition between layers of the bonded structure. The phase and amplitude of the probe response provide a direct indication of the presence and nature of bond conditions in the structure under test. The phase and amplitude response of a known acceptable portion of the structure, are nulled out by a combination of signals that are adjusted to be in phase quadrature and to have appropriate amplitudes to cancel the vector signal of the acceptable portion of the structure. Therefore, any deviation of phase or amplitude in the probe response from the normal signal vector is a sine wave signal of which the amplitude and phase are direct indications of the type and location of bondline variations. This deviation signal is represented by two DC signals which are the in-phase and quadrature phase components respectively of the vector signal representing the detected bond flaw or condition. These two constituent signals are applied to the X and Y input terminals of a CRT display to generate a dot-type presentation which is representative of the amplitude and phase, or vector tip, of the signal induced by the detected bond flaw. The noval sonic vector method of the invention utilizes a display identified herein as a sonic complex impedance plane.

In one embodiment, vector rotation is included to permit rotation of the vector tip of the detected flaw signal to any pre-selected angle in the polar coordinate system of the CRT display. In addition, a meter is included to permit selected examination of the amplitude of each of the vector constituent signals or of the composite vector signal.

In one embodiment, a programmable digital device is used to retain various bondline condition locations on the CRT display.

BACKGROUND OF THE INVENTION

This invention relates generally to an apparatus and method for nondestructively testing bonded laminar or honeycomb structures, and more particularly to a device and method for accomplishing such testing for both detection and diagnosis of bondline conditions in such structures.

It has become increasingly more common, particularly in the aircraft and space vehicle industry, to fabricate structures comprising laminated and honeycomb panels having a plurality of bonded layers of lightweight high strength materials. Such panels have multiple layers bonded together to provide sufficient strength and resistance to the otherwise destructive effects of vibration and environment to which aircraft and space vehicles are normally subjected. Consequently, it is imperative that such structural bonds be tested to determine whether or not any flaws or substandard conditions exist, and the nature of such flaws and their locations within the bonded structure.

Numerous prior art devices and methods provide means for detecting the existence of unbonds in bonded structures. For example, U.S. Pat. No. 3,453,872 to Botsco, discloses an eddy sonic inspection method which relates to inspection of panels of sandwich-type construction, by progressively exposing one surface of the panel to a fluctuating magnetic field which penetrates the panel and results in acoustical variations caused by defects. In another eddy-sonic U.S. Pat. No. 3,564,903, to Woodmansee et al, to detect flaws in a laminated structure, a magnetic transducer causes the panel to acoustically vibrate at two times the exitation frequency of energy applied to a probe. A vibration detectiing microphone, mounted directly to the panel under test, utilizes frequency filtering to provide means for indicating a signal change which represents a flaw in a bond in the material under test.

Other means for non-destructive testing of bonded structures for the purpose of detecting flaws in the bonds between the layers of the laminate, are described in a two part article by R. J. Schliekelmann in the periodical "Non-Destructive Testing", April 1972, page 79 through 84 and June 1972, page 144 through page 153.

However, in all such prior art disclosures of apparatus and methods for non-destructive testing of bonded structures, one disadvantage remains, namely, that of having no convenient way of diagnosing such flaws to precisely determine their location and also the nature of the bondline condition. The present invention combines phase and amplitude information derived from a signal responsive to the presence of a detected flaw or bondline condition in a structure, but it does so in a unique manner not heretofore known in the prior art. Although some of the aforesaid disclosures of prior art instruments and methods describe the use of the phase and amplitude of a flaw responsive test signal, none describes a method or apparatus for utilizing combined phase and amplitude information in the unique manner of the present invention, namely, the presentation of the equivalent vector on a complex impedance plane display which conveniently indicates the location and type of flaw that has been detected.

SUMMARY OF THE INVENTION

The present invention is a non-destructive bond testing method and apparatus that, like prior art methods and apparatus, utilizes impedance variation to detect the presence of flaws in the bonds between layers of a laminated structure. However, unlike prior art apparatus, the present invention utilizes both the phase and the amplitude of a signal responsive to the impedance variation to develop a vector presentation which is displayed on a cathode ray tube. This vector presentation represents the impedance characteristic of a sonic energy generating and receiving probe, the complex impedance of which is affected by bondline changes in the structure under test. A null circuit removes the zeros the vector response of a non-flawed (acceptable) portion of the structure under test so that a flawed (unacceptable) portion of the structure produces a more readily observed and diagnosed vector corresponding to impedance variation from the null point. This variation is represented on a polar coordinate display by the amplitude and angular position of the tip of the corresponding vector. The location of each vector tip provides diagnostic information regarding the location and type of detected bond flaw or condition to which it corresponds.

Sine wave oscillations of given frequency are applied to the probe and reflections from the structure under test create a standing wave, the amplitude and phase of which are dependent upon the characteristics of the structure including the presence, location and type of flaw or condition in adhesive bonds between the layers of the laminated structure. The phase and amplitude response of a portion of the structure known to be free of flaws is nulled out by a combination of signals that are, respectively, in phase quadrature and in phase with the applied oscillator signal. As a result, any deviation of phase or amplitude from a nominal signal vector in the probe response, is an additional sine wave signal, the amplitude and phase of which are direct indications of the type and location of the detected bond flaw. Two DC signals, corresponding to the in-phase and quadrature phase components, respectively, of the vector signal representing the detected bond flaw, are generated. These two component signals are applied, respectively, to the X and Y input terminals of a cathode ray tube to generate a dot-type presentation which is representative of the tip of the vector signal induced by the detected bond flaw. The polar coordinate location of this vector tip is indicative of the detection of a flaw, and is also indicative of the location and nature of the flaw.

One embodiment of the present invention also includes a circuit to enable rotation of the vectors to any pre-selected angle in the polar coordinate system of the display. In addition, a meter is included to enable selective examination of the amplitude of the component quadrature signals, and also of the composite vector signal. In said one embodiment of the present invention, a programmable, digital circuit is included to permit retention of the vector tip presentation on the cathode ray tube display after the probe is removed from the location of the corresponding bond flaw. This circuit-imposed display memory permits recordation and enhances diagnosis of the bond flaws of the structure under test without requiring the user to make note of the locations of respective vector tips during the testing process. In addition, this memory feature permits test calibration and signal standardization directly on the display.

It is therefore an object of the present invention to provide a non-destructive bond testing method and apparatus which permit both detection and diagnosis of bond flaws in bonded structures.

It is another object of the present invention to provide a non-destructive bond testing method and apparatus that combine phase and amplitude information derived from a sonic probe to generate a vector signal response that may be displayed on a cathode ray tube for both detection and diagnosis of adhesive bond flaws in bonded structures.

It is still another object of the present invention to provide a method and apparatus for detecting and diagnosing flaws in the bonds between layers of a laminated structure and which includes means for the display of the complex impedance function representative of detected flaws.

It is still another object of the present invention to provide a bond flaw detection and diagnosis instrument for displaying the vector response of a sonic energy testing device on a cathode ray tube in a polar coordinate system, and wherein the amplitude and phase of the vector response is indicative of the location and nature of bond flaws in the structure under test.

BRIEF DESCRIPTION OF THE DRAWINGS

Other objects and advantages of the present invention will become apparent from the following detailed description when considered in conjunction with the accompanying drawings in which:

FIG. 8, comprising

DETAILED DESCRIPTION OF A PREFERRED EMBODIMENT

Figure 1:
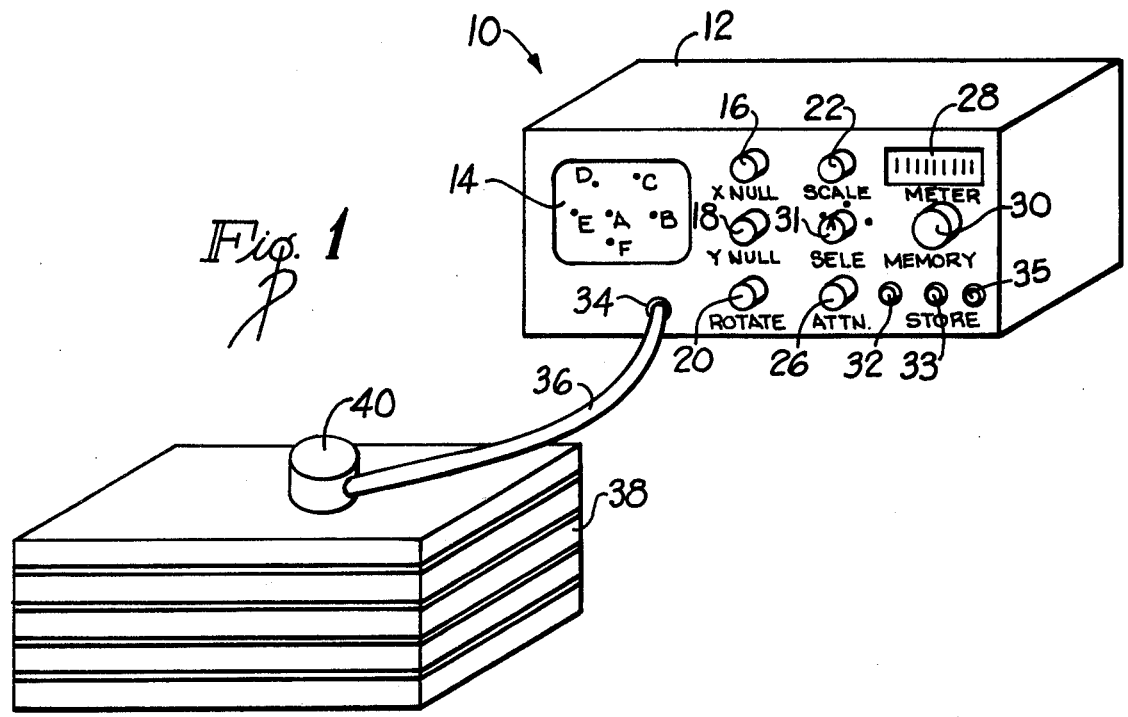
FIG. 1 is an isometric view of the present invention shown being used for non-destructive testing of a multi-layered laminar.

Referring now to FIG. 1 there is shown therein an embodiment of the present invention being utilized for non-destructive testing of a multilayered structure to permit detection and diagnosis of bond flaws that may be located between the various layers. As illustrated in FIG. 1, the embodiment 10 of the invention is assembled in a panel type chassis 12 which includes a cathode ray tube display 14 and a plurality of panel dials, including X-null dial 16, Y-null dial 18, rotate dial 20, scale dial 22, attenuation dial 26, and memory dial 30. Also included on the front panel of chassis 12 is a meter 28, a select switch 31, and erase, store, and identify buttons 32, 33 and 35, respectively. The present invention employs a sonic energy transceiver probe 40 which is connected to the invention by means of front panel connector 34 and cable 36. Under normal operating conditions, probe 40 is applied in direct contact to the surface of the structure under test which includes a multilayer structure 38.

The dots labeled A through F that appear on display 14 of the invention, represent the tips of vector signals on a polar coordinate system wherein in each such vector tip represents the phase and amplitude of a complex impedance which corresponds to a deviation signal induced by a flaw in an adhesive bond between the surfaces of laminated structure 38. Typically, vector tip A represents the nulled vector tip of a signal derived when the probe is placed on the structure at an area that is free of flaws in adhesive bonds throughout all the layers at that area. In order to place vector tip A at the origin of the coordinate system utilized in the display, X and Y null dials 16 and 18 are utilized as described below in conjunction with FIGS. 7 and 8. Vector tip B represents the deviation signal that, typically, would be displayed if the probe is lifted up off the surface of the structure 38. Vector tips C through F represent the deviation signals that would be displayed for disbonds in the first, second, third and fourth layers respectively, as indicated in the lower left-hand corner of FIG. 1. One of the advantages of the present invention becomes apparent from the fact that the angle of each vector tip is dependent upon the depth of the layer in which the detected bond flaw occurs. For example, in the illustrative display indicated in FIG. 1, vector tip C, which represents an un-bond in the first layer of the structure 38, is approximately 70° from the X axis while vector D is approximately 110°, vector E is approximately 180° and vector F is approximately 260° from the X axis. Thus an operator using the present invention, may, at a glance at the cathode ray tube display, determine the location of each detected bond flaw in a simple and expedient manner by merely observing the angle between the vector represented by the displayed vector tip and the axes of the polar coordinate system. Although some prior art bond testing devices may provide some indication of phase information with respect to sonic energy received signals from a probe of the type illustrated in FIG. 1, the diagnostic capability provided by the present invention is either absent or is a far more difficult and inconvenient process that requires a complex interpretation scheme.

Rotate dial 20 provides a means of rotating all the vector tips for increased convenience of diagnosis and for calibration and standardization purposes. Scale dial 22 is used to set the meter 28 on scale. Attenuation dial 26 provides a means of varying the amplitude of the vector tips so that the distance between each tip and the origin of the polar coordinate display may be adjusted for optimum ease of interpretation.

The present invention also provides means for observing the relative amplitude of each vector tip signal and of the horizontal and vertical deflection component signals of each vector signal, for additional diagnostic purposes. Any one of three signals may be selected to be applied to the meter 28 by three position switch 31. Memory dial 30 is used in conjunction with a programmable, digital circuit described below in conjunction with FIG. 7, which permits retention of vector tips on the cathode ray tube display even after the probe is removed from the portions of the structure at which the corresponding bond flaws are detected.

Figure 7:
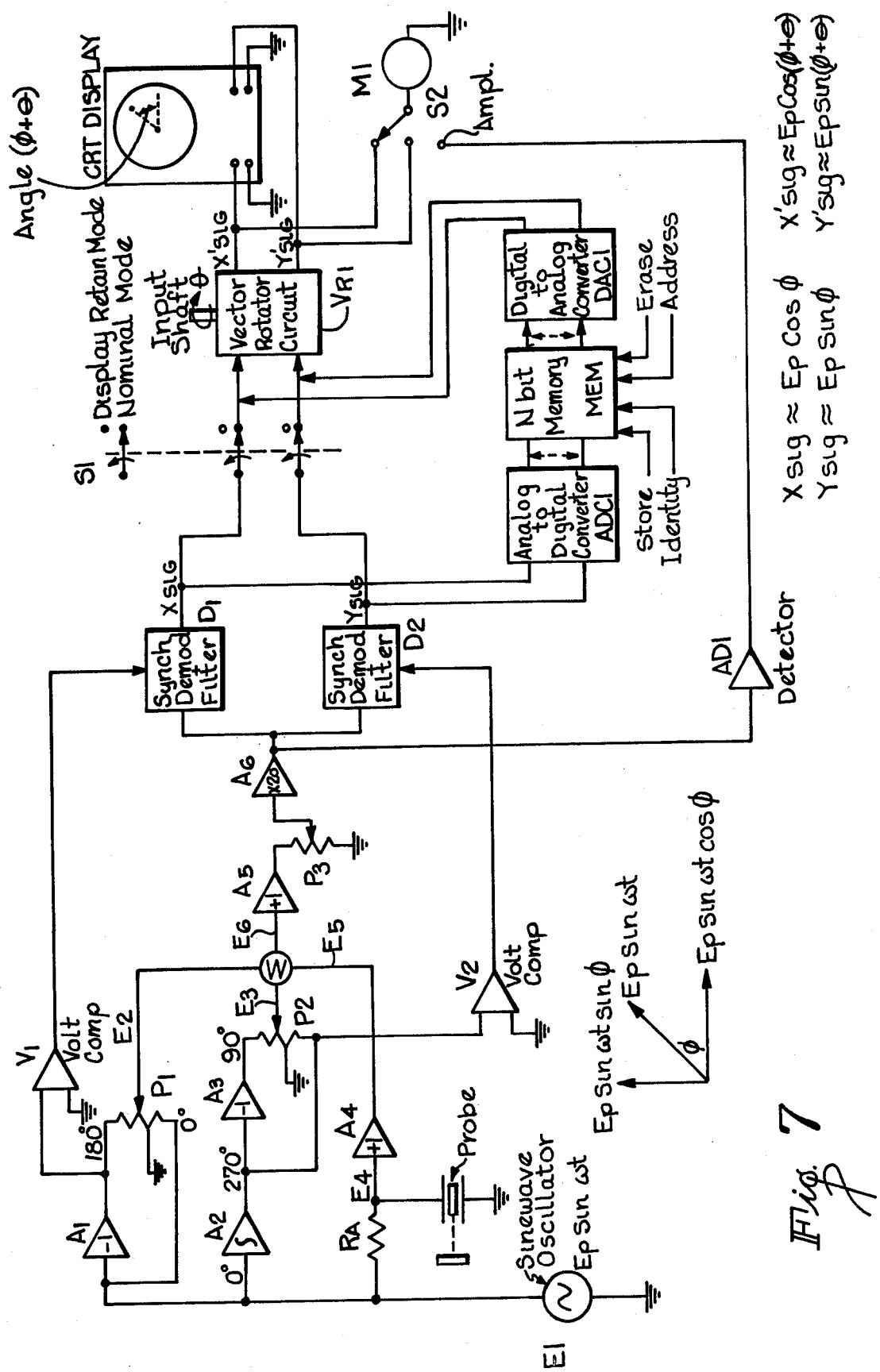
FIG. 7 is a block diagram representation of the invention.

Dial 30 is a memory address selection dial which permits the user to select any one of a number of addresses in an N-bit memory (see FIG. 7). Thus by means of memory dial 30, digital representations of vector tips may be selectively stored in an N-bit memory at different address locations and then reapplied to the cathode ray tube display and also to the meter when the memory dial is returned to the corresponding address at a later time. This unique, programmable, digital circuit and memory dial feature of the present invention, permits initial calibration as well as the retention and diagnosis of vector tip signals on the cathode ray tube display and also on the meter, after the probe is removed from the portion of the structure at which point the bond flaw was detected. Memory dial 30 is used in conjunction with store push-button switch 33 which, when pressed by the user, causes storage of the current probe signal in the memory at the address location corresponding to the setting of memory dial 30. Erase button 32 deletes an addressed and stored vector tip from the display, while identify button 35 adds an alphanumeric code identification to selected vector tips on the display.

Figures 2, 3, 5:
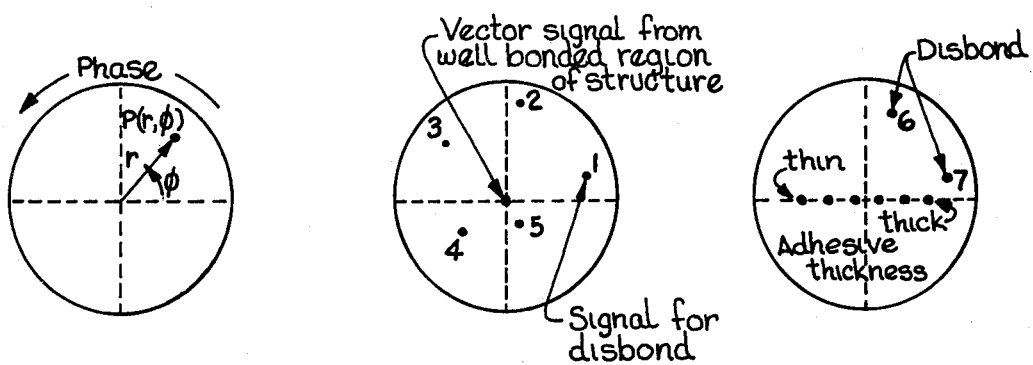
FIG. 2 is an enlarged view of a sound vector presentation on a complex impedance plane in a polar coordinate system.
FIG. 3 is a sonic impedance plane response to disbonds at various depths in a multilayered adhesive bonded laminar structure.
FIG. 5 is another sonic impedance plane response to disbonds and adhesive thickness variations in a bonded laminar structure.

FIG. 2 illustrates a sound wave vector presented in polar coordinate form on the sonic complex impedance plane display of the present invention. As indicated in FIG. 2, the vector signal $P(r,\phi)$ is a vector represented on the display by a vector tip, of which the distance from the origin of the coordinate system of the display, (represented by r) is a function of the amplitude of the vector signal, and of which the angle $\phi$ with respect to the positive horizontal axis, is representative of the phase angle of the vector signal. Thus, FIG. 2 illustrates, in polar coordinate form, a sound vector presentation on a complex impedance display, with the amplitude (r) of the vector shown in radial direction from the center of the screen, and the phase ($\phi$) of the vector shown as an angle from the X axis. In actual practice it is convenient to display only the tip of the vector as represented by the point $P(r,\phi)$ in FIG. 2.

Figure 4:
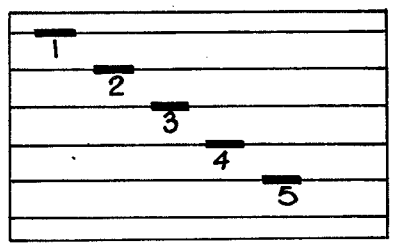
FIG. 4 is a sectional view of a laminar structure corresponding to the impedance plane response of FIG. 3.

FIG. 3 is a typical CRT display of a vector response for five vector tip signals corresponding to five disbonds illustrated in a sectional view of a laminar structure in FIG. 4. As illustrated in FIG. 3, the sonic impedance plane response to the disbonds at various depths in a multilayered adhesive bonded laminar structure, includes a plurality of vector tips that differ from one another in both phase and amplitude. This difference in phase and amplitude provides means by which an operator may diagnose the detected bond flaw by merely observing the display. By way of example, vector tip No. 1 corresponds to disbond No. 1 at the first depth in the sectional view of FIG. 4.

As a result, the operator realizes that a disbond exists somewhere below the probe in the area of the structure to which the probe is applied, and that the flaw is at a specific depth in the structure. The vector tip at the center of the display corresponds to a signal from a well-bonded region of the structure, which by means of the nulling circuits to be discussed in conjunction with FIGS. 7 and 8, has been adjusted to appear at the origin of the sonic impedance plane, displayed in polar coordinate form on the CRT of the invention.

Figure 6:
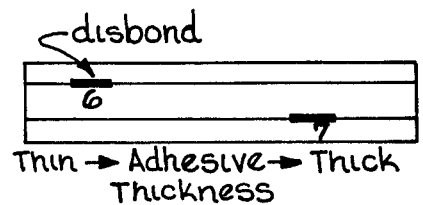
FIG. 6 is a sectional view of a laminar structure corresponding to the impedance plane response of FIG. 5.

FIGS. 5 and 6 illustrate a similar presentation, but in this case the sonic impedance plane response corresponds to disbonds and adhesive thickness variations in a bonded laminar structure. Actual experimentation has verified that adhesive thickness variations, which affect cohesive bond strength, produce vector tip indications at characteristic locations. Other types of structure anomalies, such as the degree of adhesive cure, adhesive degradation and porosity, also produce characteristic signature on the CRT screen. Thus this type of nondestructive bond testing device provides a powerful method for inspecting bonded structures by detecting and diagnosing the flaws. The invention provides means to locate the layer at which the bond flaw occurs, assess the cause of the flaw, determine whether it is non-bond or a disbond and whether it is an anomalous condition that would be detrimental to the structure being tested.

The manner in which an apparatus of the present invention may be designed and fabricated, will be best understood by reference to FIGS. 7 and 8 which comprise a block diagram and schematic diagram, respectively, of an embodiment of the present invention. As shown in the functional block diagram of FIG. 7, a sine wave oscillator E1 produces an output signal which may be mathematically described as $E_p \sin \omega t$. This output signal is applied to voltage comparator V1, inverting amplifier A1, potentiometer P1, integrating amplifier A2, and a combination of resistor RA and the sonic energy probe which is placed in contact with the structure under test.

The probe is usually comprised of a resonant piezoelectric element to transmit and receive sonic energy; however, other types of probes can be used. Probes of the piezoelectric type are discussed in detail in the book entitled "Sonics" by Heuter and Bolt, published by Wiley and Sons, 1955, and therefore need not be discussed in any detail herein. The probe may be represented by an equivalent resonant circuit, the complex impedance of which is affected by the physical characteristics of the specimen under test. As a result, the complex impedance of the probe, and thus the phase and amplitude of the signal E4 developed at the probe terminal, is representative of the structure under test and, more specifically, of the nature and location of bonds and bond flaws between the various layers of the laminate structure under test. Signal E4 contains the phase and amplitude data from which vector component signals may be applied to the cathode ray tube display as will be described below.

Signal E4 is applied to a buffer amplifier A4, the output signal of which, E5, is applied to a summing junction $\sigma$. It will be understood that the signal E5 has a phase and amplitude and a corresponding signal vector associated with it, even when the probe is applied to a portion of the structure that contains acceptable bonds. Summing junction $\sigma$ provides means for cancelling out or nulling the vector signal associated with a known acceptable portion of the laminate structure under test. This nulling means utilizes signals E2 and E3, which are also applied to summing junction $\sigma$. Signals E2 and E3 are set equal to the in-phase and quadrature phase components of the vector signal derived from the probe when it is applied to a known acceptable portion of the specimen under test. To develop signal E2, signal E1, that is the output signal of the sine wave oscillator, is applied directly to one terminal of potentiometer P1. The output signal of inverting amplifier A1, which is 180° out of phase with sine wave oscillator output signal E1, is applied to the other terminal of potentiometer P1. The center tap of potentiometer P1 is grounded so that signal E2 represents the X axis or abscissa component of a nulled vector signal that may be adjusted in amplitude and polarity by means of potentiometer P1.

In order to develop the quadrature component signal E3, sine wave oscillator output signal E1 is applied to integrating amplifier A2. The output signal of amplifier A2 is 270° out of phase with oscillator signal E1. This 270° phase-shifted signal is applied to one terminal of potentiometer P2. It is also applied to inverting amplifier A3, the output signal of which is 90° out of phase with oscillator signal E1. This 90° phase-shifted signal is applied to the other terminal of potentiometer P2. The center tap of potentiometer P2 is grounded so that the signal E3 represents the Y axis or ordinate component of a nulled vector signal that may be adjusted in amplitude and polarity by means of potentiometer P2.

Thus by means of adjustment of potentiometers P1 and P2, X axis component signal E2 and Y axis component signal E3, may be adjusted to provide any vector signal appropriate to null out that portion of signal E5 that corresponds to a known acceptable portion of the test specimen, that is, a portion that is free of bond flaws. Consequently, the signal at the output side of summing junction $\sigma$, namely, signal E6, after appropriate adjustment of potentiometers P1 and P2, represents the deviation of the complex impedance of the probe as a result of the detection of a flaw in the adhesive bonding between the layers of the laminate structure under test. Signal E6 is applied to a buffer amplifier A5, the output signal of which is applied to one terminal of potentiometer P3. The other end of potentiometer P3 is grounded so that the center tap terminal of potentiometer P3 represents an attenuated form of signal E6. This attenuation capability is provided to permit sensitivity adjustment and calibration of the vector signal that is eventually applied to the cathode ray tube display to be discussed below.

The output signal available at the center tap terminal of potentiometer P3, is applied to amplifier A6. The output signal of A6 is applied to a pair of synchronous demodulator and filter circuits D1 and D2, respectively, and also to an amplitude detector AD1. Detector AD1 provides an output signal that corresponds to the amplitude of signal E6. This amplitude representative signal is applied to one of three terminals of switch S2, any one terminal of which may be selectively connected to meter M1 which provides the user with an additional source of diagnostic information as will be discussed below.

The purpose of synchronous demodulator and filter circuits D1 and D2, is to develop the vector component signals of test signal E6. The manner in which these component signals are generated within circuits D1 and D2 will be described hereinafter in detail in conjunction with FIG. 8. However, it will be understood that in order to develop the vector component signals of signal E6 it is necessary to provide reference signals to circuits D1 and D2. These reference signals, namely, an in-phase demodulator reference signal and a quadrature phase demodulator reference signal, are produced by voltage comparators V1 and V2, respectively.

Voltage comparators V1 and V2 are implemented in the form of operational amplifiers without feedback circuits. One input terminal is grounded and the other input terminal provides an input signal dependent upon sine wave oscillator signal E1. Therefore the output signal of voltage comparators V1 and V2 is a square wave, the amplitude limits of which correspond to the peak voltage limits of the operational amplifiers comprising comparators V1 and V2, and the polarity of which depends upon whether the variable input signal is greater than or less than ground potential. In other words, comparators V1 and V2 produce output signals, the amplitudes of which remain constant at one polarity or another depending upon whether or not the variable input signal has crossed the zero voltage axis. In the case of voltage comparator V1, the variable signal applied to the non-grounded input terminal is an inverted form of signal E1. In the case of voltage comparator V2, the variable signal applied to the non-grounded input terminal is in quadrature phase relation to sine wave oscillator signal E1. Thus, the respective variable input signals to voltage comparators V1 and V2 are 90° out of phase.

The output signals of demodulator and filter circuits D1 and D2, respectively, are applied to terminals of a multi-pole switch S1. Multi-pole switch S1 is used to select either one of two modes for display on a cathode ray tube of the invention. In one mode, namely, the display retain mode, the X and Y signal components of vector signal E6 are applied to a digital circuit comprising: Analog-to-digital converted ADC1, N-bit memory MEM, and digital to analog converted DAC1. This programmable digital circuit is used to retain digital representations of the component signals of E6 during the entire test of a laminated structure so that a plurality of bond-flaw-induced vector signals may be retained for concurrent display on the cathode ray tube. In the second mode selectable by multi-pole switch S1, namely, the nominal mode, the X and Y signal components of vector signal E6 bypass the programmable digital circuit so that only the vector signal being sensed by the probe is displayed.

In either case, the X and Y component signals developed by demodulator and filter circuits D1 and D2, are applied separately to a vector rotator circuit VR1. Vector rotator circuit VR1 includes an input shaft which permits the user of the invention to rotate the polar coordinate system of the complex impedance plane display an additional angle $\theta$ to enhance the diagnostic process provided by the invention. The X and Y component signals available at the output of circuits D1 and D2 respectively, may be mathematically described as $Ep \cos \phi$ and $Ep \sin \phi$, and respectively, where $\phi$ represents the phase characteristic of the vector signal E6. By means of vector rotator circuit VR1, the signals that are applied to the CRT display, namely, component signals X' and Y', may be described mathematically as $Ep \cos (\phi+\theta)$ and $Ep \sin (\phi+\theta)$ respectively, where $\theta$ is the added angle of rotation provided by the vector rotator circuit VR1.

The output signals of vector rotator circuit VR1, namely, X' and Y', are applied, respectively, to the X axis input terminals and Y axis input terminals of a CRT display as shown in the upper right-hand portion of FIG. 7. As shown in FIG. 7, the signal components X' and Y' may also be applied to two additional terminals of multi-terminal switch S2 so that they may be individually selected to be applied to meter M1 for an indication of their respective amplitudes.

The above discussion of the block diagram of FIG. 7 provides a general overview of the manner in which the phase and amplitude characteristics of a signal representative of a complex impedance variation in a sonic probe, induced by the occurrence of a bond flaw in a structure under test, are developed and displayed in a polar-coordinate system by means of the present invention. Reference shall now be made to FIG. 8 for a more detailed schematic representation of the invention which will enable those of ordinary skill in the art to which the present invention pertains to more fully understand the design and operation of the invention to a degree sufficient to enable them to make and use the invention.

In FIG. 8 all the resistor values are in Ohms ±5% and 0.25 watts minimum. All capacitor values are in microfarads ±20%, 30 volt minimum. All the diodes shown are 1N4148 diodes and all the transistors shown are 2N2484 transistors, unless otherwise specified.

Figure 8B:
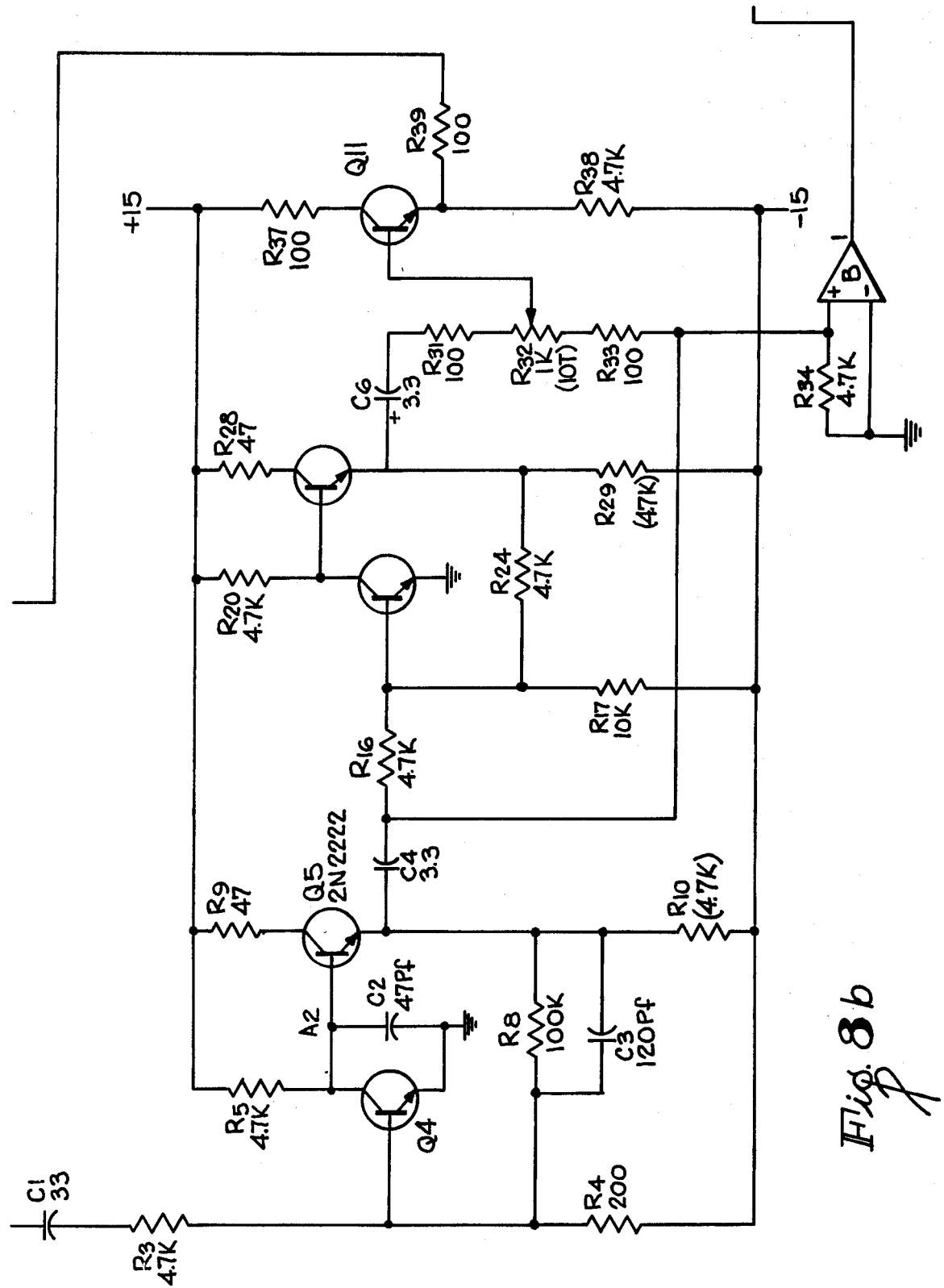
FIGS. 8a, 8b, 8c, and 8d, is a detailed schematic drawing of the invention.
Figure 8A:
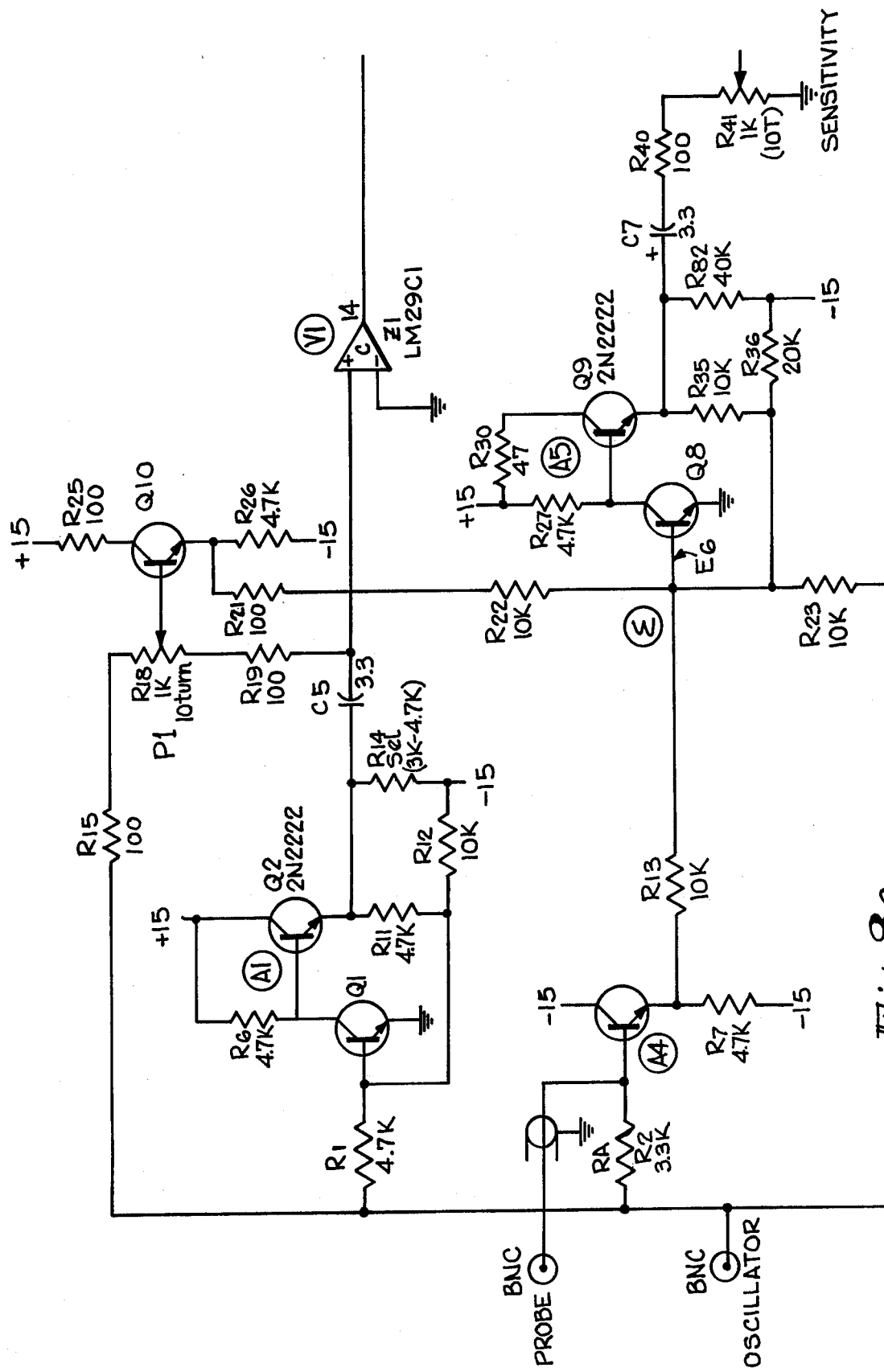

Starting with FIG. 8a, it will be seen that a sine wave oscillator is connected to the circuit of the present invention by means of a BNC connector, the center pin of which is connected, (see the upper left-hand corner of FIG. 8a), to amplifier A1 which comprises transistors Q1 and Q2 and associated resistors to establish the proper bias voltages in the amplifier. A1, as previously noted in conjunction with FIG. 7, is an inverting amplifier. The output signal of A1 is applied to potentiometer P1 which is used to null out the nominal value of a vector signal corresponding to a known portion of the structure that is free of bond flaws. The oscillator signal is also applied directly to the other end of potentiometer P1 through resistor R15 as shown in the upper left-hand corner of FIG. 8a.

Oscillator signal E1 is also applied to integrating amplifier A2, which comprises resistors Q4 and Q5 along with corresponding resistors and capacitors to provide the circuit equivalent of an integrating function. The output signal of amplifier A2, available at the emitter junction of Q5, is in quadrature phase relationship to the signal E1, available at the output of the sine wave oscillator. This quadrature phase signal, is applied directly to one terminal of potentiometer circuit comprising resistors R31, R32, and R33 as shown in the lower right-hand portion of FIG. 8b.

The output signal of the integrating amplifier A2 is also applied to inverting amplifier A3, the circuit of which is virtually identical to the circuit of inverting amplifier A1, previously discussed. Inverting amplifier A3 shifts the phase of the output signal of integrating amplifier A2, an additional 180° to provide a 90° phase shifted signal with respect to the output signal of the sine wave oscillator. This 90° phase shifted signal is applied to the other terminal of potentiometer P2. The output signals of potentiometers P1 and P2 are applied to emitter follower transistor circuits Q10 and Q11 respectively, the emitter junctions of which are connected, through appropriate resistors, to summing junction $\sigma$ at the base junction of transistor Q8. Also applied to summing junction $\sigma$ is the buffered, probe output signal E5, which is applied to buffer amplifier A4 before it reaches the summing junction $\sigma$.

As previously discussed in conjunction with FIG. 7, potentiometer circuits P1 and P2 provided a means for cancelling or nulling out the nominal phase and amplitude of the vector signal developed by the probe when it is applied to a portion of the laminar structure that contains no bond flaws. Potentiometers P1 and P2 accomplish this nulling function by providing two quadrature-phase-related signals, one of which is in-phase with oscillator sine wave signal E1 and one of which is 90° out of phase with oscillator sine wave signal E1 and by providing means for adjusting each such quadrature component in both amplitude and polarity as required to achieve the nulling function. Thus, when the potentiometers P1 and P2 are properly adjusted to achieve this nulling effect, the signal at summing junction $\sigma$ is equal to zero, and corresponds to a vector tip at the origin of the cathode ray tube display as long as the probe is applied to portions of the structure under test that are free of bond flaws.

On the other hand, if the probe is applied to a portion of the structure that does include adhesive bonding that is flawed in some respect, the signal developed at summing junction $\sigma$ deviates, in phase and/or amplitude, from the nominal signal that corresponds to an acceptable portion of the structure. It is this deviation signal that may be described as a vector, the tip of which is displayed as a dot on the cathode ray tube of the present invention and it is the polar coordinate location of this vector tip that provides information for diagnosis of each detected bond flaw in the structure under test.

The circuitry illustrated in FIG. 8b to the right of summing junction $\sigma$, is used to provide quadrature-related component signals of the deviation vector signal which are applied to the horizontal and vertical deflection terminals of a cathode ray tube that input, respectively, to the horizontal and vertical deflection circuits so that they may be displayed to the user.

To the immediate right of summing junction σ in FIG. 8b is shown a buffer amplifier, A5, which comprises transistors Q8 and Q9. The output of A5 is applied to a sensitivity potentiometer P3 which is used to control the amplitude of the deviation signal before it is applied to the remainder of the circuit of the present invention. The output signal of sensitivity potentiometer P3 is applied, through a limiting resistor R44, to the base junction of transistor Q12, which in combination with transistors Q13 and Q14, and the associated circuit, provides an amplifier, A6, having a voltage gain of approximately 20 (see FIG. 8c).

Amplitude detection circuit AD1 is connected to the emitter terminal of transistor Q14 through capacitor C13, and comprises transistor Q20 and the network comprising resistors R90 and R91 and capacitor C30. Capacitor C30 stores the average value of the vector signal which can be selectively applied to meter M1 by switch S2.

The output signal of amplifier A6, which is available at the emitter junction of transistor Q14, is applied to capacitor C13 and resistor R56. R56 is connected to ground through diode CR1 which has a negative temperature coefficient to provide a temperature compensating factor in the invention. The output signal of capacitor C13 is applied to the base junctions of transistors Q15 and Q16, respectively, which are used as emitter follower-buffers for applying the deviation signal to two separate phase demodulator circuits. These circuits develop the signals that are eventually applied to the horizontal and vertical deflection circuits of the cathode ray tube. These two signals, denoted X and Y respectively, are DC signals the amplitudes of which are proportional to the in-phase and quadrature phase components respectively of the deviation vector signal. The manner in which these DC signals are developed will now be discussed.

As previously discussed in conjunction with FIG. 7, voltage comparators V1 and V2 are used to develop an in-phase demodulator reference signal and a quadrature-phase demodulator reference signal, respectively. Each voltage comparator is an operational amplifier without a feedback circuit. The negative input terminal of each such operational amplifier is connected to ground potential and the positive terminal is in the case of comparator V1 connected to the output circuit of amplifier A1, and in the case of comparator V2 is connected to the output circuit of amplifier A2. The input signals to voltage comparators V1 and V2 are 90° out of phase with respect to each other and 180° and 270° out of phase, respectively, with respect to signal E1 of the sine wave oscillator to which the circuit is connected. As a result, the output signal of voltage comparator V1 is a square wave, the polarity of which changes when the sine wave E1 crosses the zero voltage axis. The V1 output signal is a square wave which is in-phase with the oscillator sine wave signal. On the other hand, the output signal of voltage comparator V2, is a square wave, the polarity of which is dependent upon the zero voltage axis crossings of a signal that is in phase-quadrature with the output of the sine wave oscillator.

The in-base demodulator reference signal is applied to the base junction of transistor Q17 and the quadrature demodulator reference signal is applied to the base junction of transistor Q18. These two transistors, Q17 and Q18, are used as switches which are in an on configuration when the base-to-emitter junction is positively biased and in an off configuration when the base-to-emitter junction is negatively biased. Q17 and Q18 transfer the respective input signals, applied to the collector junctions, to an RC circuit comprising a 20 K-Ohm resistor and 0.12 microfarad capacitor when Q17 and Q18 are in their off configurations. On the other hand, when they are turned on by a positive base-to-emitter bias voltage, the emitters of Q17 and Q18 are grounded and the voltage applied to each collector is held at about ground potential through the respective transistor.

Accordingly, the voltages stored in capacitors C18 and C19 respectively, represent an average value of the product of the square wave applied to the base junction of the switching transistor and the sine wave applied to the collector junction of the switching transistor. If the sine wave and the square wave are in-phase, the average value stored by the capacitor C18 or C19 is a maximum. On the other hand, if these two signals are 90° out of phase, the average value is zero. The in-phase DC component signal X, is proportional to the amplitude of the deviation signal and to the cosine of the phase difference between the deviation signal and the sine wave oscillator signal. Similarly, the quadrature DC component signal Y, is proportional to the amplitude of the deviation signal and to the sine of the phase difference between the deviation signal and the sine wave oscillator signal. These two average value DC signals, available at capacitor C18 and C19 respectively, are applied to amplifiers Z10 and Z11 respectively, which produce DC signals at their respective output terminals. The various phase relationships between the demodulator reference signals and the deviation signal and the corresponding DC component signals X and Y, are illustrated in graphical form in FIG. 10.

As previously noted in the discussion of FIG. 7, signals X and Y may be rotated in angle by means of vector rotator circuit VR1 before these signals are applied to the horizontal and vertical deflection circuits, respectively, of a cathode ray tube display. The means by which this rotation is accomplished is illustrated in schematic form in FIG. 8d. This transformation of sin $\phi$ into sin $(\phi+\theta)$ with $\theta$ being the additional angle of rotation imparted by the vector rotator circuit VR1 and the transformation of cos $\phi$ to cos $(\phi+\theta)$, are accomplished by vector rotator circuit VR1 by means of the following trigonometric identities:

$$\sin(\phi+\theta) = \sin\phi\cos\theta + \cos\phi\sin\theta$$

$$\cos(\phi+\theta) = \cos\phi\cos\theta - \sin\phi\sin\theta$$

The X and Y signals are applied to a dual ganged sine/cosine potentiometer. In addition, the signals X and Y are also applied to this potentiometer after they are inverted by means of operational amplifiers Z2 and Z3, respectively. The output side of the sine/cosine potentiometer provides four signals, namely, X cos $\theta$, X sin $\theta$, Y cos $\theta$, and Y sin $\theta$. Thus, all the products necessary to achieve the above trigonometric identities to produce the terms sin $(\phi+\theta)$ and cos $(\phi+\theta)$, which are hereinafter designated Y' and X' respectively, are available at the output terminals of the ganged sine/cosine potentiometer. The various output signals are buffered in amplifiers Z4, Z5, Z6 and Z7, and then applied to the appropriate polarity terminals of operational amplifiers Z8, Z12 and Z13 to achieve the additions and subtractions to fulfill the mathematical functions of the above indicated trigonometric identities. The signals applied to the terminals identified as horizontal deflection and vertical deflection respectively, are the above indicated rotated vector component signals X' and Y'. Signals X' and Y' are available to the horizontal and vertical deflection input terminals respectively, of a cathode ray tube display as discussed previously in conjunction with FIG. 7.

Figure 8C:
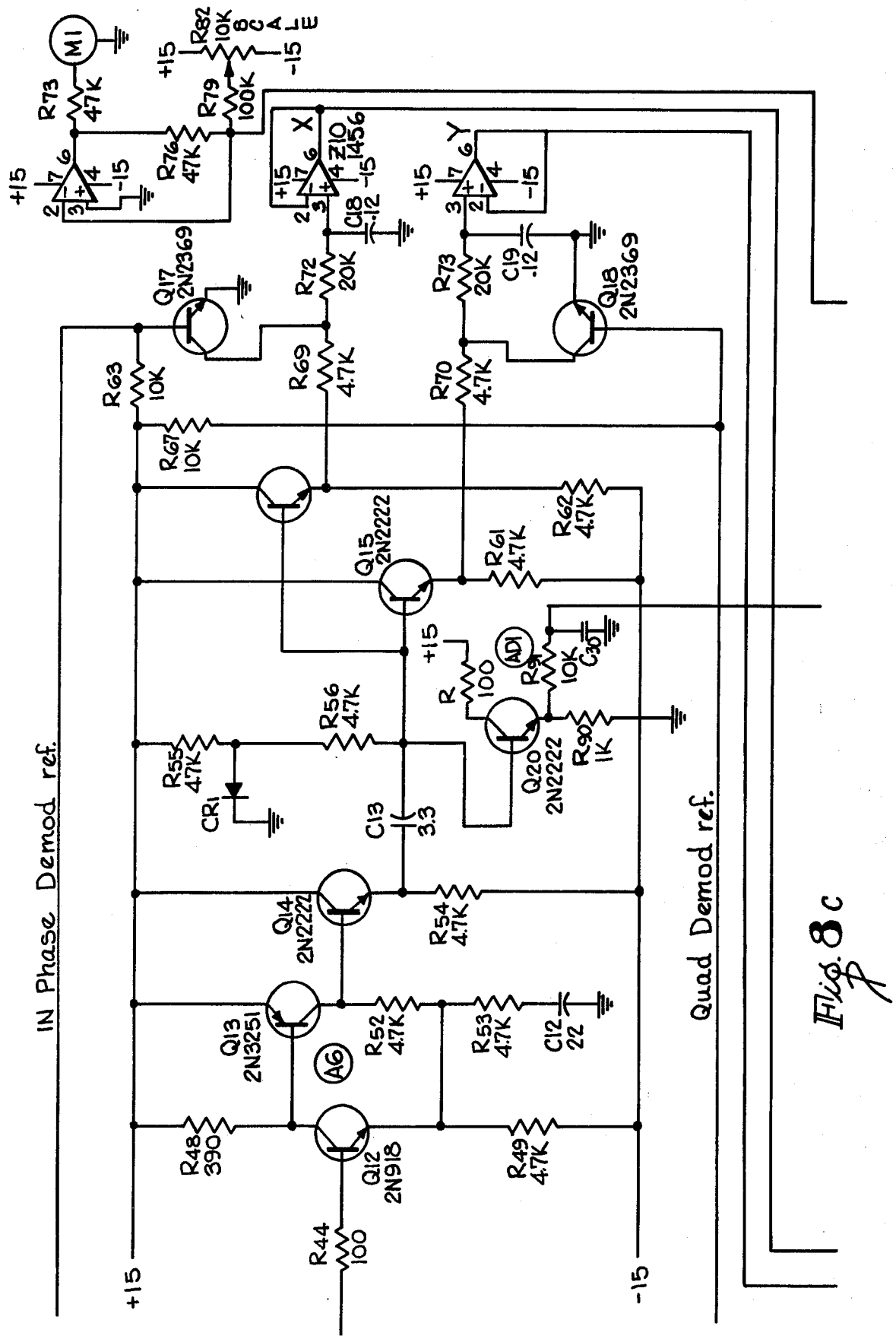
Figure 8D:
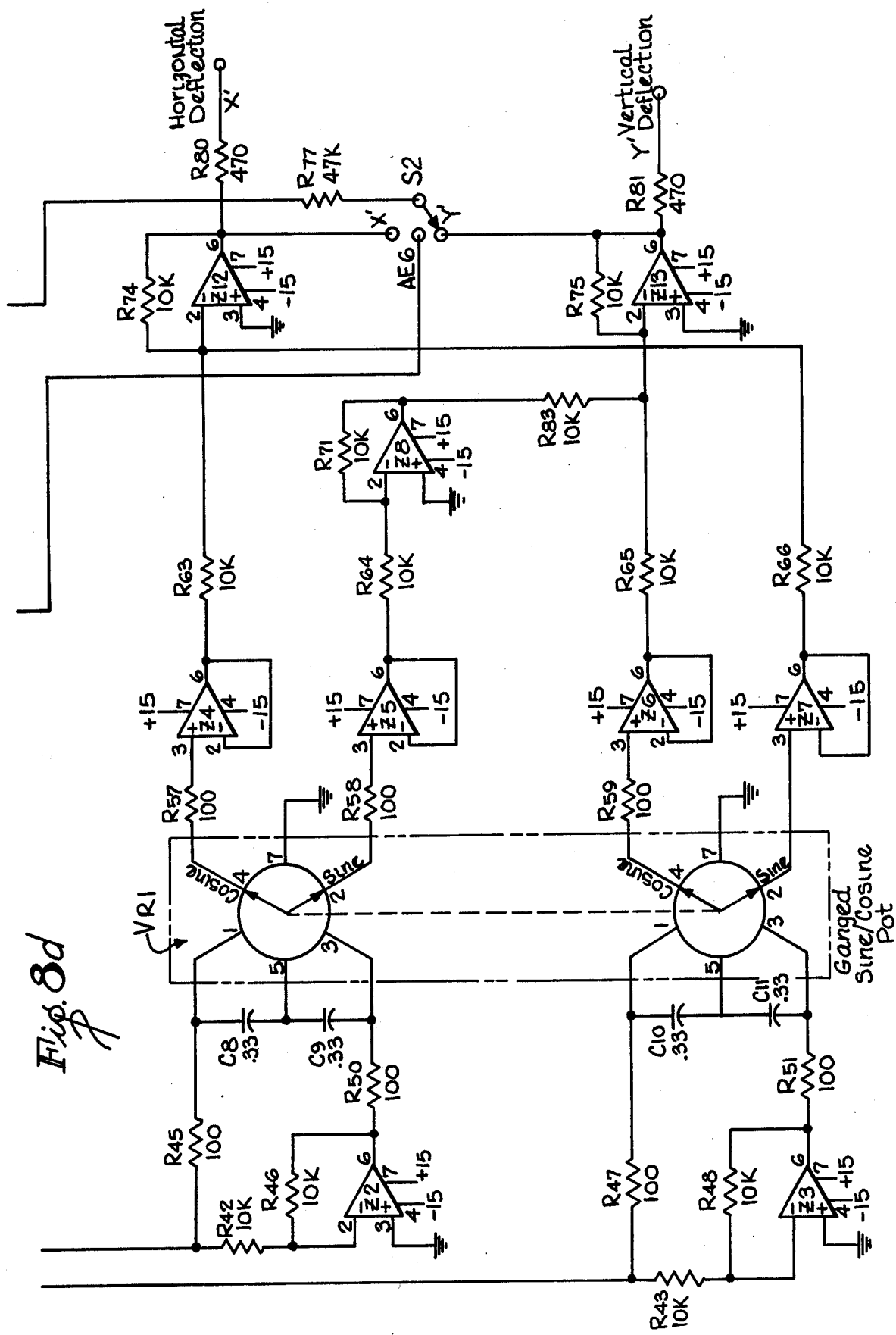
Figure 9:
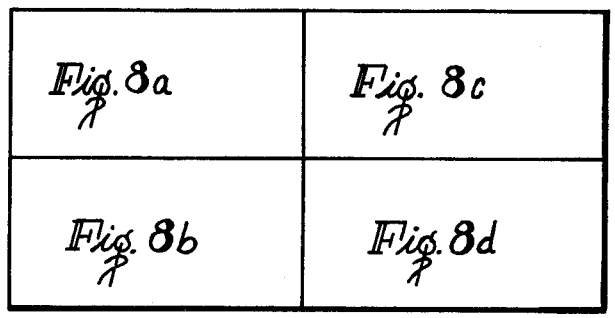
FIG. 9 is an interface drawing that shows the manner in which FIG. 8 should be used.

As shown in FIG. 8c, the circuit of the present invention also includes means for applying a number of different signals to a meter M1 through summing operational amplifier Z9. There are two signals applied to the input terminals of amplifier Z9, namely, a meter adjust signal developed at potentiometer R82, which is used to bring the meter on scale, and a signal which is derived from the output terminal of switch S2. As illustrated in FIG. 8d, switch S2 has three input terminals, any one of which may be selected for application to the meter circuit. The three input signals are X', Y', and the detected amplitude signal AE6 which is derived from detection circuit AD1 to which is applied the composite deviation signal E6, as previously discussed in conjunction with FIG. 7.

Figure 10:
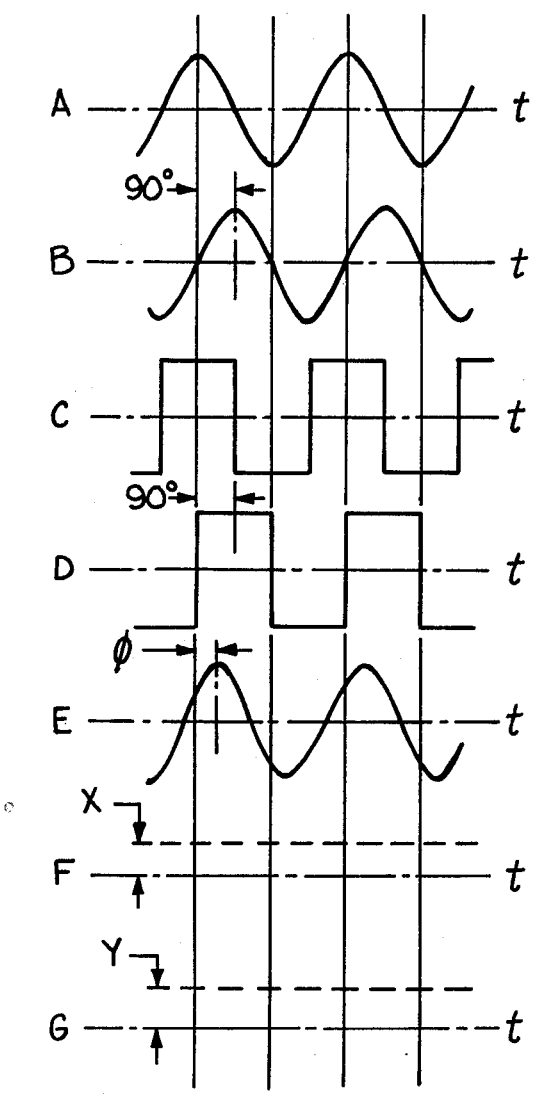
FIG. 10 is a graph of various signals utilized in the invention to extract phase and amplitude characteristics of signals resulting from the detection of bond flaws in a test specimen.

Referring now to FIG. 10, which comprises seven graphs representative of signals occurring at various locations in the circuit of the present invention, graph A is the signal applied to voltage comparator V1 which is in-phase with inverted sine wave oscillator signal E1, graph B is the signal applied to voltage comparator V2 which is in quadrature phase relation with signal E1, graphs C and D are the in-phase and quadrature phase demodulator reference signals respectively, graph E is an example of a vector deviation signal E6 resulting from the detection of a bond flaw, and graphs F and G represent DC component signals X and Y produced by synchronous demodulator and filter circuits D1 and D2.

It will be seen that the input signals to the respective voltage comparators V1 and V2, are 90° out of phase and that the output signals are square waves and also 90° out of phase. It will be seen further that for purposes of illustration, the angle $\phi$ in graph E is assumed to be approximately 45°, which causes the X and Y DC component signals (shown in graphs F and G, respectively), to be approximately equal in amplitude because the sine of 45° is equal to the cosine of 45°. As previously discussed in conjunction with FIG. 7, the DC component signals of the flaw-induced deviation vector signal, are each dependent upon the amplitude and phase of the received probe signal and, therefore, dependent upon the complex impedance of the probe.

It will now be understood that what has been disclosed herein is a novel process and apparatus for detection and diagnosis of bond flaw conditions in a multilayered structure where the respective layers are bonded together, (usually adhesively).

The invention utilizes a novel complex impedance plane display in which vector tips, representative of deviation signals derived from bond flaw detection, are presented in a polar coordinate display. The amplitude and angle of rotation of each such vector tip is representative of characteristics of detected bond flaws that may be readily observed and diagnosed with the current invention. Also disclosed is a programmable, digital circuit that may be selectively utilized for initial calibration with a material reference sample by retaining vector tip responses on a cathode ray tube display to further enhance the diagnostic capabilities provided by the invention. Also disclosed is the use of a meter in conjunction with said complex impedance plane display for suppressing or accentuating test signals from a detected bond flaw or anomaly in the material being tested. This suppression or accentuation may be accomplished in the present invention by rotating the vector angle until one component signal is positioned along either the horizontal or vertical axis of the display so that the meter responds to the other component signal on the other axis. Similarly, if one wishes to accentuate and quantitatively read out the signal amplitude characteristic for a particular anomaly, the vector of that characteristic may be rotated to the horizontal or vertical axis and the meter used to respond to only that signal's amplitude.

Although a specific embodiment of the invention has been disclosed herein, it will now be apparent to those having ordinary skill in the art to which the invention pertains, that many other embodiments of the invention may be utilized. For example, in view of applicants' teaching herein disclosed it will now be apparent that there may be variations in the sequence of steps and in the apparatus of the invention. It will also now be apparent that the disclosed apparatus may be utilized for many other purposes in addition to detection and diagnosis of adhesive bond flaws between the layers of a laminated structure. By way of example, the disclosed apparatus may be useful for analyzing the composition or condition of many types of materials such as liquids, gases and other solid materials. One particular potential application is the continuous monitoring of the properties of liquids or gases as they move through pipes. Another useful application for the present invention is in the medical field for detection and diagnosis of pathological conditions such as the physical characteristics of tissue or bone structure in selected areas of the body. Accordingly, the invention is not to be limited except as defined by the appended claims.

We claim:

1. An improved apparatus for non-destructively detecting and diagnosing flaws and other bondline conditions between the bonded layers of multilayered bonded structures, the apparatus having a sonic energy transceiver probe for physical contact with a surface of the structure, the complex impedance of the probe being indicative of the location of a detected bond flaw, the apparatus also having a source for generating a steady state sonic energy signal of known frequency, the signal being input to the probe, the phase and amplitude of the output signal of the probe being indicative of the complex impedance of the probe; the improvement comprising:

means for processing a probe output signal to produce component signals representative of the relative phase and amplitude of said probe output signal, and means for displaying said component signals to produce a visual indication of the relative phase and amplitude of the said probe output signal whereby the location of the detected bond flaw is determined.

2. An improved apparatus as defined in claim 1, further comprising:

means for nulling the probe output signal corresponding to the complex impedance of said probe when said probe is in contact with said structure at a portion thereof known to be free of bond flaws.

3. An improved apparatus as defined in claim 1, wherein said displaying means comprises:

a cathode ray tube display having vertical and horizontal deflection circuits to which said component signals are applied, respectively.

4. An improved apparatus as defined in claim 1, wherein said processing means comprises:
a pair of phase sensitive demodulators, each such demodulator generating a direct current signal, the amplitude of one of said direct current signals being proportional to the amplitude of said probe output signal and to the cosine of the phase angle difference between said probe output signal and said sonic energy signal, the amplitude of the other of said direct current signals being proportional to the amplitude of said probe output signal and to the sine of the phase angle difference between said probe output signal and said sonic energy signal.

5. An improved apparatus as defined in claim 1, further comprising:
means for selectively modifying said component signals whereby the relative phase of said probe output signal is changed by a selected angle.

6. An improved apparatus as defined in claim 1, further comprising:
means for storing signal manifestations representative of said component signals and for selectively applying said signal manifestations to said displaying means for displaying said visual indications after said probe has been removed from said structure.

7. An improved apparatus as defined in claim 1, further comprising:
a meter, means for generating a direct current signal proportional to the amplitude of said probe output signal and independent of the phase of said probe output signal, and
means for selectively applying said component signal and said direct current signals to said meter.

8. A process for non-destructively detecting and diagnosing flaws and other bondline conditions between the bonded layers of a multilayered bonded structure, utilizing a sonic energy transceiver probe to be place in direct contact with a surface of the structure, the complex impedance of the probe being indicative of the location of a detected bond flaw; and also utilizing a source for generating a steady state sonic energy signal of known frequency, the phase and amplitude of the output signal of the probe being indicative of the complex impedance of the probe; the process comprising the steps of:
processing a probe output signal to produce component signals representative of the phase and amplitude of said probe output signal, and
displaying said component signals to produce a visual indication of the phase and amplitude of said probe output signal whereby the location of a detected bond flaw is determined.

9. The process as defined in claim 8, further comprising the step of:
nulling the probe output signal corresponding to the complex impedance of said probe when said probe is in contact with said structure at a portion known to be free of bond flaws.

10. The process as defined in claim 8, wherein said displaying step comprises the step of:
applying said component signals respectively to the vertical and horizontal deflection circuits of a cathode ray tube display.

11. The process as defined in claim 8, in which said processing step comprises the steps of:
generating a first direct current signal the amplitude of which is proportional to the amplitude of said probe output signal and to the cosine of the phase angle difference between said probe output signal and said sonic energy signal, and
generating a second direct current signal, the amplitude of which is proportional to the amplitude of said probe output signal and to the sine of the phase angle difference between said probe output signal and said sonic energy signal.

12. The process as defined in claim 8, further comprising the step of:
selectively modifying said component signals whereby the phase of said probe output signal is changed by a selected angle.

13. The process as defined in claim 8, further comprising the steps of:
storing signal manifestations representative of said component signals, and
selectively applying said signal manifestations to said displaying means for displaying said visual indication after said probe has been removed from said structure.

14. The process as defined in claim 8, further comprising the steps of:
generating a direct current signal proportional to the amplitude of said probe output signal and independent of the phase of said probe output signal, and
selectively applying said component signals and said direct current signal to a meter.

15. An apparatus for detecting and diagnosing structural characteristics in a test specimen, said apparatus comprising:
a source for generating a steady state reference signal,
means for applying said reference signal to said test specimen and for receiving a response signal from said test specimen, said response signal having phase and amplitude parameters indicative of said structural characteristics,
means for generating DC signals, the amplitudes of which represent, respectively, the amplitudes of quadrature-phase related component signals of a vector indicative of said response signal phase and amplitude parameters, and
means for displaying said DC signals in a vector tip presentation on a coordinate plane, the position of each such vector tip being representative of a vector between the origin of said coordinate plane and the vector tip.

16. An apparatus as defined in claim 15, further comprising:
means for rotating said vector tip presentation through a pre-selected angle.

17. An apparatus as defined in claim 15, further comprising:
means for rotating a selected vector tip until said vector tip lies on an axis of said coordinate plane.

18. An apparatus as defined in claim 15, further comprising:
means for determining the relative amplitude of a selected one of said DC signals.

19. An apparatus as defined in claim 15, further comprising:
means for selectively storing manifestations of said Dc signals at selected locations in an electrical memory device,
means for selectively applying said stored manifestations to said displaying means whereby vector tips or alpha-numeric code representations thereof are displayed after said reference signals are removed from said test specimen.

20. A process for detecting and diagnosing structural characteristics in a test specimen, the process comprising the steps of:
generating a steady state reference signal,
applying said reference signal to said test specimen,
receiving a response signal from said test specimen, said response signal having phase and amplitude parameters indicative of said structural characteristics,
generating DC signals, the amplitudes of which represent, respectively, the amplitudes of quadrature-phase related component signals of a vector indicative of said response signal phase and amplitude parameters, and
displaying said DC signals in a vector tip presentation on a coordinate plane, the position of each such vector tip being representative of a vector between the origin of said coordinate plane and the vector tip.

21. The process of claim 20, further comprising the step of rotating said vector tip presentation through a preselected angle.

22. The process as defined in claim 20, further comprising the step of rotating a selected vector tip until said vector tip lies on an axis of said coordinate plane.

23. The process as defined in claim 20, further comprising the step of:
determining the relative amplitude of a selected one of said DC signals.

24. The process as defined in claim 20, further comprising the step of:
selectively storing manifestations of said DC signals at selected locations in an electrical memory device,
selectively displaying said stored manifestations whereby vector tips or alpha-numeric code representations thereof are displayed after said reference signal is removed from said test specimen.

25. An improved apparatus for non-destructively detecting and diagnosing flaws and other bondline conditions between the bonded layers of multilayered structures, the apparatus having a sonic energy transceiver probe for physical contact with a surface of the structure, the complex impedance of the probe being indicative of the location of a detected bond flaw, the apparatus also having a source for generating a steady state sonic energy signal of known frequency, the signal being input to the probe, the phase and amplitude of the output signal of the probe being indicative of the complex impedance of the probe; the improvement comprising:
means for processing a probe output signal to produce component signals representative of the relative phase and amplitude of said probe output signal,
means for displaying said component signals to produce a visual indication of the relative phase and amplitude of the said probe output signal whereby the location of the detected bond flaw is determined,
means for nulling the probe output signal corresponding to the complex impedance of said probe when said probe is in contact with said structure at a portion thereof known to be free of bond flaws,
means for selectively modifying said component signals whereby the relative phase of said probe output signal is changed by a selected angle,
means for storing signal manifestations representative of said component signals and for selectively applying said signal manifestations to said displaying means for displaying said visual indications after said probe has been removed from said structure,
a meter, means for generating a direct current signal proportional to the amplitude of said probe output signal and independent of the phase of said probe output signal, and means for selectively applying said component signals and said direct current signal to said meter.

26. Am improved apparatus as defined in claim 25, wherein said displaying means comprises:
a cathode ray tube display having vertical and horizontal deflector circuits to which said component signals are applied, respectively.

27. An improved apparatus as defined in claim 25, wherein said processing means comprises:
a pair of phase sensitive demodulators, each such demodulator generating a direct current signal, the amplitude of one of said direct current signals being proportional to the amplitude of said probe output signal and to the cosine of the phase angle difference between said probe output signal and said sonic energy signal, the amplitude of the other of said direct current signals being proportional to the amplitude of said probe output signal and to the sine of the phase angle difference between said probe output signal and said sonic energy signal.

28. A process for non-destructively detecting and diagnosing flaws and other bondline conditions between the bonded layers of multilayered structures, utilizing a sonic energy transceiver probe to be placed in direct contact with a surface of the structure, the complex impedance of the probe being indicative of the location of a detected bond flaw; and also utilizing a source for generating a steady state sonic energy signal of known frequency, the phase and amplitude of the output signal of the probe being indicative of the complex impedance of the probe; the process comprising the steps of:
processing a probe output signal to produce component signals representative of the phase and amplitude of said probe output signal,
displaying said component signals to produce a visual indication of the phase and amplitude of said probe output signal whereby the location of a detected bond flaw is determined,
nulling the probe output signal corresponding to the complex impedance of said probe when said probe is in contact with said structure at a portion known to be free of bond flaws,
selectively modifying said component signals whereby the phase of said probe output signal is changed by a selected angle,
storing signal manifestations representative of said component signals,
selectively applying said signal manifestations to said displaying means for displaying said visual indication after said probe has been removed from said structure,
generating a direct current signal proportional to the amplitude of said probe output signal and independent of the phase of said probe output signal, and selectively applying said component signals and said direct current signal to a meter.

29. The process as defined in claim 28, wherein said displaying step comprises the step of:

applying said component signals respectively to the vertical and horizontal deflection circuits of a cathode ray tube display.

30. The process as defined in claim 28, in which said processing step comprises the steps of:

generating a first direct current signal the amplitude of which is proportional to the amplitude of said probe output signal and to the cosine of the phase angle difference between said probe output signal and said sonic energy signal, and generating a second direct current signal, the amplitude of which is proportional to the amplitude of said probe output signal and to the sine of the phase angle difference between said probe output signal and said sonic energy signal.

31. An apparatus for detecting and diagnosing sructural characteristics of a material under test, said apparatus comprising:

a source for generating a steady state reference signal, means for applying said reference signal to said material and for receiving a response signal from said material, said response signal having phase and amplitude parameters indicative of said structural characteristics, means for generating DC signals, the amplitudes of which represent, respectively, the amplitudes of quadrature-phase related component signals of a vector indicative of said response signal phase and amplitude parameters, means for displaying said DC signals in a vector tip presentation on a coordinate plane, the position of each such vector tip being representative of a vector between the origin of said coordinate plane and the vector tip, means for rotating said vector tip presentation through a pre-selected angle, means for determining the relative amplitude of a selected one of said DC signals, means for selectively storing manifestations of said DC signals at selected locations in an electrical memory device, and means for selectively applying said stored manifestations to said displaying means whereby vector tip representations are displayed after said reference signals are removed from said test specimen.

32. A process for detecting and diagnosing structural characteristics of a material under test, the process comprising the steps of:

generating a steady state reference signal, applying said reference signal to said material, receiving a response signal from said material, said response signal having phase and amplitude parameters indicative of said structural characteristics, generating DC signals, the amplitudes of which represent, respectively, the amplitudes of quadrature-phase related component signals of a vector indicative of said response signal phase and amplitude parameters, displaying said DC signals in a vector tip presentation on a coordinate plane, the position of each such vector tip being representative of a vector between the origin of said coordinate plane and the vector tip, rotating said vector tip presentation through a preselected angle, determining the relative amplitude of a selected one of said DC signals, selectively storing manifestations of said DC signals at selected locations in an electrical memory device, and selectively displaying said stored manifestations whereby vector tips or alpha-numeric code representations of such are displayed after said reference signal is removed from said test specimen.

* * * * *

UNITED STATES PATENT AND TRADEMARK OFFICE
CERTIFICATE OF CORRECTION

PATENT NO. : 4,215,583
DATED     : August 5, 1980
INVENTOR(S) : Botsco et al

It is certified that error appears in the above—identified patent and that said Letters Patent is hereby corrected as shown below:

Column 1, line 34, change "noval" to --novel--.
Column 7, line 26, change "$\sigma$" to --$\Sigma$--.
Column 7, line 30, change "$\sigma$" to --$\Sigma$--.
Column 7, line 34, change "$\sigma$" to --$\Sigma$--.
Column 8, line 1, change "$\sigma$" to --$\Sigma$--.
Column 10, line 30, change "$\sigma$" to --$\Sigma$--.
Column 10, line 31, change "$\sigma$" to --$\Sigma$--.
Column 10, line 33, change "$\sigma$" to --$\Sigma$--.
Column 10, line 48, change "$\sigma$" to --$\Sigma$--.
Column 10, line 56, change "$\sigma$" to --$\Sigma$--.
Column 10, line 65 change "$\sigma$" to --$\Sigma$--.
Column 11, line 3, change "$\sigma$" to --$\Sigma$--.

Signed and Sealed this

Twenty-fourth Day of March 1981

[SEAL]

Attest:

RENE D. TEGTMEYER

Attesting Officer        Acting Commissioner of Patents and Trademark